(12) United States Patent
Monga et al.

(10) Patent No.: US 9,706,970 B2
(45) Date of Patent: Jul. 18, 2017

(54) IDENTIFYING KIDNEY STONE COMPOSITION FROM MEDICAL IMAGING

(71) Applicant: THE CLEVELAND CLINIC FOUNDATION, Cleveland, OH (US)

(72) Inventors: Manoj Monga, Shaker Hts., OH (US); Giovanni S. Marchini, Sao Paulo (BR)

(73) Assignee: The Cleveland Clinic Foundation, Cleveland, OH (US)

(*) Notice: Subject to any disclaimer, the term of this patent is extended or adjusted under 35 U.S.C. 154(b) by 206 days.

(21) Appl. No.: 14/445,124

(22) Filed: Jul. 29, 2014

(65) Prior Publication Data
US 2015/0031992 A1   Jan. 29, 2015

Related U.S. Application Data

(60) Provisional application No. 61/859,371, filed on Jul. 29, 2013.

(51) Int. Cl.
| *A61B 5/05* | (2006.01) |
| *A61B 6/00* | (2006.01) |
| *A61B 6/03* | (2006.01) |
| *G06T 7/00* | (2017.01) |
| *G06F 19/00* | (2011.01) |

(52) U.S. Cl.
CPC ............ *A61B 6/5217* (2013.01); *A61B 6/032* (2013.01); *A61B 6/50* (2013.01); *G06F 19/321* (2013.01); *G06F 19/345* (2013.01); *G06F 19/3443* (2013.01); *G06T 7/0012* (2013.01); *G06T 2207/10081* (2013.01); *G06T 2207/20076* (2013.01); *G06T 2207/30084* (2013.01)

(58) Field of Classification Search
CPC ......... A61B 6/5217; A61B 6/50; A61B 6/032; G06F 19/345; G06F 19/3443; G06F 19/321; G06T 7/0012; G06T 2207/10081; G06T 2207/20076; G06T 2207/30084
USPC ........................... 600/407–430; 382/128–132
See application file for complete search history.

(56) References Cited

U.S. PATENT DOCUMENTS

| 8,311,181 B2 | 11/2012 | Thomsen et al. |
| 8,364,240 B2 | 1/2013 | Krauss |

(Continued)

OTHER PUBLICATIONS

Basiri et al., "What is the State of the Stone Analysis Techniques in Urolithiasis", Urology Journal, Spring 2012, vol. 9, No. 2, pp. 445-454.

*Primary Examiner* — Sanjay Cattungal
(74) *Attorney, Agent, or Firm* — Tarolli, Sundheim, Covell & Tummino LLP

(57) ABSTRACT

Systems and methods are provided for determining the composition of a kidney stone from a medical image. A feature extractor is configured to provide a plurality of features from the medical image. The plurality of features includes either a pair of an attenuation values including a first attenuation value from a first location in or on the kidney stone and a second attenuation value from a second location in or on the kidney stone or a function of the first and second attenuation values. The second location is spatially distinct from the first location. A classifier is configured to select one of a plurality of classes for the kidney stone from the plurality of features. Each class represents a specific constituent material. A user interface is configured to display the class to a user in a human comprehensible form.

20 Claims, 2 Drawing Sheets

(56) References Cited

U.S. PATENT DOCUMENTS

2007/0249933 A1* 10/2007 Krauss ................ A61B 5/4869
  600/425
2014/0236488 A1* 8/2014 Brown .................. A61B 6/505
  702/19

* cited by examiner

IDENTIFYING KIDNEY STONE COMPOSITION FROM MEDICAL IMAGING

RELATED APPLICATIONS

The present application claims priority to U.S. Provisional Patent Application Ser. No. 61/859,371 filed Jul. 29, 2013 entitled IDENTIFYING KIDNEY STONE COMPOSITION FROM MEDICAL IMAGING, the entire contents of which being incorporated herein by reference in its entirety for all purposes.

FIELD OF THE INVENTION

The present invention relates to systems and methods for surgical monitoring and, in particular, is directed to systems and methods for identification of the composition of kidney stones from a computed tomography scan.

BACKGROUND OF THE INVENTION

A kidney stone, also known as a renal calculus, is a solid concretion or crystal aggregation formed in the kidneys from dietary minerals in the urine. Urinary stones are typically classified by their location in the kidney (nephrolithiasis), ureter (ureterolithiasis), or bladder (cystolithiasis), or by their chemical composition. For example, kidney stones can be formed from calcium-containing substances, struvite, uric acid, or other compounds.

Nephrolithiasis is a worldwide health problem responsible for significant economic cost to society and serious effects on quality of life. Over the past few decades, it had been shown that stone disease incidence and prevalence steadily increased, attributed presumably to changes in diet and lifestyle. Uric acid stones contribute substantially to that ascending curve and may be related to chronic the growing epidemic of obesity and diabetes mellitus.

SUMMARY OF THE INVENTION

In accordance with an aspect of the present invention, a non-transitory computer readable medium stores machine executable instructions that, when executed by an associated processor, provide a system for determining the composition of a kidney stone from a medical image. A feature extractor is configured to provide a plurality of features from the medical image. The plurality of features includes either a pair of an attenuation values including a first attenuation value from a first location in or on the kidney stone and a second attenuation value from a second location in or on the kidney stone or a function of the first and second attenuation values. The second location is spatially distinct from the first location. A classifier is configured to select one of a plurality of classes for the kidney stone from the plurality of features. Each class represents a specific constituent material. A user interface is configured to display the class to a user in a human comprehensible form.

In accordance with another aspect of the present invention, a system is provided for determining the composition of a kidney stone. The system includes a computed tomography imager, a processor, an output device, and a non-transitory computer readable medium. The medium stores machine executable instructions and is operatively connected to the processor. The instructions include an imager interface configured to receive a computed tomography image from the computed tomography imager and provide a bone-windowed computed tomography image from the received computed tomography image. A feature extractor is configured to provide a plurality of features from the bone-windowed computed tomography image. The plurality of features includes either a pair of an attenuation values, including a first attenuation value from a first location in or on the kidney stone and a second attenuation value from a second location in or on the kidney stone, or a function of the first and second attenuation values. The second location is spatially distinct from the first location. A classifier is configured to select one of a plurality of classes for the kidney stone, with each class representing a specific constituent material. A user interface configured to display the class to a user in a human comprehensible form at the output device.

In accordance with still another aspect of the present invention, a method is provided for determining the composition of a kidney stone. A computed tomography (CT) scan of a region of interest containing a kidney stone is obtained at an associated CT imaging system. Each of a first attenuation value, representing a central region of the kidney stone, and a second attenuation value, representing at least one peripheral region of the kidney stone, are determined from the CT scan. A class is selected from a plurality of classes each representing a possible composition of the kidney stone, using at least the first and second attenuation values. The selected class is provided to a user in a human comprehensible form.

BRIEF DESCRIPTION OF THE DRAWINGS

The foregoing and other features of the present invention will become apparent to those skilled in the art to which the present invention relates upon reading the following description with reference to the accompanying drawings, in which.

DETAILED DESCRIPTION OF THE INVENTION

In accordance with an aspect of the present invention, systems and methods are provided for non-invasive determination of kidney stone composition from medical imaging. Treatment methods for kidney stones can vary according to composition. For example, if a physician can determine that a stone is composed of uric acid, non-surgical methods of treating the stone can be utilized.

Noncontrast computed tomography is the gold-standard imaging modality to identify calculi in the collecting system. Stone size, location and hardness may be precisely acquired from NCCT and may assist in treatment decision making. Stone composition also plays an important role in the disease management. Unfortunately, the different materials from which stones can form can look similar in computed tomography images. For example, the attenuation values of calcium containing stones significantly overlap, making them difficult to distinguish in an X-ray image. The inventors have determined, however, that the spatial homogeneity of the stones does vary, and this variance can be exploited to distinguish among different kidney stone compositions.

Figure 1:
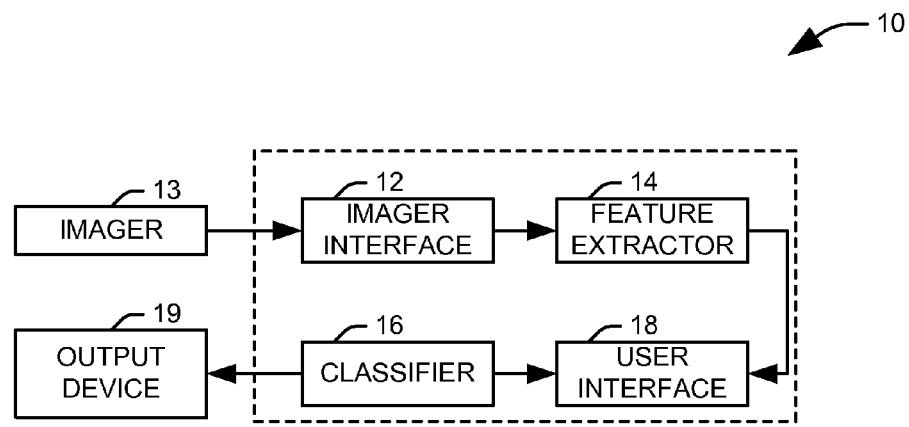
FIG. 1 illustrates a system for determining a composition of a kidney stone from a computed tomography image.

FIG. 1 illustrates a system 10 for determining a composition of a kidney stone from a medical image in accordance with an aspect of the present invention. It will be appreciated that multiple components 12, 14, 16, and 18 of the illustrated system 10 can be implemented as dedicated hardware, software instructions stored on one or more non-transitory computer readable media, or a combination of hardware and software. An imager interface 12 is configured to receive a one of more medical images taken of a patient from an imaging system 13. In one implementation, the input interface 12 can comprise machine readable instructions for receiving the scan from an associated CT imager, formatting the CT scans for other portions of the system and adjusting a displayed dynamic range of the image to a range appropriate for viewing bone, referred to as a "bone window." In an alternative implementation, the input interface 12 is configured to interact with a medical database or other automated data source to obtain the medical image.

The medical image data is provided to a feature extractor 14. In accordance with an aspect of the present invention, a plurality of features used in predicting the composition of a kidney stone includes a pair of a color values drawn from preselected, spatially distinct locations within the kidney stone, or a function of the pair of attenuation values. By a "color value", it is meant a digital value representing the brightness, hue, or saturation at a particular location in the image, and can include, for example, the grayscale brightness or red, blue, or green component of a given pixel or pixels at the location. In a CT image, the measured attenuation values would provide the color values for that imaging modality. It will be appreciated that the features are intended to represent the homogeneity of the stone, and thus by "spatially distinct," it is meant that the two locations are separated by distance at least five percent of the diameter of the kidney stone. Additional features can also be employed in classifying the kidney stone, such as a volume, diameter of the selected cross-section, a largest transverse diameter, and a variance of the color values in the selected cross-section.

In one example, the features can include a first color value near a center of the kidney stone and a second color value near a periphery of the kidney stone and a function of the first and second color values. To this end, the feature extractor 14 can utilize a transverse slice of the CT having the two largest transverse diameters, and determine a region of interest with near the center of cross-section of the kidney stone within the slice. An average of the pixels within the defined central region of interest can be used as the first color value. One or more regions of interest that include an outside edge of the cross-section can be used in the same manner to provide the second color value.

In one implementation, a feature set containing the first and second color values can be used for identifying the material of the kidney stone. However, one or more functions of the first and second color values can be utilized as features in place of or in addition to the first and second color values. Potential features can include, for example, a ratio of first and second color values, a difference between the first and second color values, a relative difference (e.g., a ratio of the difference to one of the values), or a normalized difference (a ratio of the difference to a largest transverse diameter of the stone.

The parameters derived for the plurality of features are provided to a classifier 16, which is configured to select a class representing the composition of the stone from the plurality of features. In the illustrated implementation, the classifier 16 is implemented as a support vector machine that distinguishes between calcium-containing and uric acid stones according to a largest transverse diameter of the stone and a difference between the first color value, representing the color at the center of the stone, and the second color value, representing a color at the periphery of the stone. It will be appreciated, however, that the predictive model 16 can utilize any appropriate classification or regression model, such as an artificial neural network, a regression analysis, a statistical classifier, a decision tree, a rule-based classifier, or any other appropriate predictive model. A user interface 18 is configured to provide the selected class to a user in a human comprehensible form via an associated output device 19. Specifically, the user interface 18 interacts with a display, printer, speaker, or other appropriate output device to provide the calculated likelihood of post-procedure morbidity to a user.

The inventors hypothesized that differences in the spatial distribution of core and periphery HU values and appearance in bone windows could distinguish stone composition. In an initial analysis, uric acid and calcium oxide stones were examined, as these two compositions that have an increasing prevalence in our population. To avoid potential factors that might affect attenuation measurement in noncontrast computed tomography (NCCT), such as partial-volume inaccuracies, the study sample included only stones four millimeters or larger, which is larger than the three millimeter collimation size used in the study.

During the study, a single urologist, blinded to stone composition, reviewed all of the NCCT images to avoid discrepancies in measurement technique. Magnification of the stone and its surroundings was used to allow precise measurement of stone parameters. The transverse diameter of the stone on each slice was measured in millimeters. The image slice containing the two largest transverse diameters of the stone was used to characterize stone size and to measure absolute Hounsfield Unit (HU) value. The absolute HU attenuation value for each stone was calculated by measuring a central region of interest (ROI) for each stone (25 pixels per ROI) on 0.5 mm² in the previous chosen slice to provide a core HU. The same was done in the two outside edges of the largest stone diameter to provide a Periphery HU. By dividing the core HU of each stone by its largest transverse diameter, the HU density (HUD) value was obtained. The stone volume was also calculated from measurements of NCCT by using the two largest axial diameters and the largest reconstructed coronal diameter, with V=length (cm)×width (cm)×depth (cm)×z×0.167. After measurements, the same urologist used the previously selected image slice and changed the NCCT window from abdominal to bone in order to study stone characteristics and discrepancies in both acquisitions.

The main elements analyzed were stone size, volume, core HU, periphery HU, absolute and relative HU difference (between core and periphery HU), HUD, and finally the difference between stone compositions in NCCT abdominal and bone window. Within the same stone composition, patients were also divided in three groups according to maximum stone diameter: 4-10 mm; and >10 mm. A Chi-square or Fisher Exact Test was used to compare categorical variables. One-way analysis of variance (ANOVA) was used to compare the analyzed elements between different stone size groups within the same stone composition. Independent sample Students' T-Test was used to compare all analyzed parameters between the two stone compositions. Spearman's correlation test was used to determine the correlation between HU values (core and periphery) and stone size and volume for both stone compositions. The level of significance was set at p<0.05. The results are summarized in Table 1.

Figure 3:
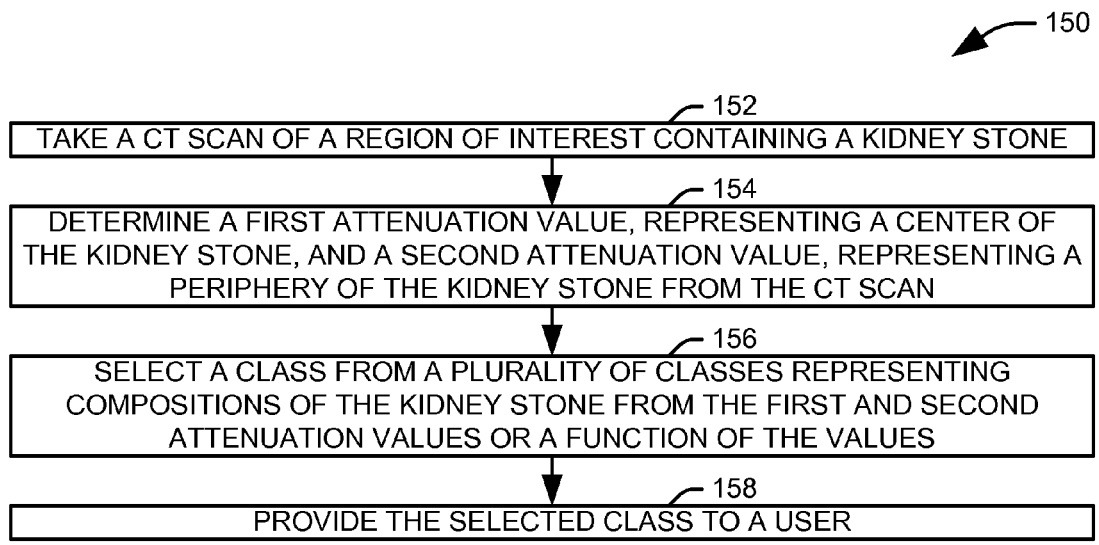
FIG. 3 illustrates another method for determining a composition of a kidney stone from medical imaging.

FIG. 3 illustrates a method 150 for determining a composition of a kidney stone from medical imaging in accordance with an aspect of the present invention. At 152, a computed tomography (CT) scan is taken of a region of

TABLE 1

|  | n | Core HU Mean ± SD | Range | Periphery HU Mean ± SD | Range | Absolute HU Difference Mean ± SD | Range | Relative HU Difference Mean ± SD | Range | HUD Mean ± SD | Range |
|---|---|---|---|---|---|---|---|---|---|---|---|
| Uric Acid |  |  |  |  |  |  |  |  |  |  |  |
| Overall | 47 | 523 ± 106 | 285-759 | 382 ± 73 | 244-582 | 140 ± 88 | −29-503 | 25.4 ± 13.4% | −5.5-67% | 78 ± 45 | 12-208 |
| ≤10 mm | 32 | 518 ± 111 | 285-751 | 374 ± 73 | 244-558 | 144 ± 93 | −29-503 | 26.1 ± 13.8% | −5.5-67% | 99 ± 40 | 48-208 |
| >10 mm | 15 | 532 ± 97 | 420-759 | 399 ± 70 | 272-582 | 130 ± 85 | −35-341 | 23.6 ± 13.5% | −6.5-49.8% | 34 ± 14 | 12-59 |
| Intra UA comparison* |  | 0.91 |  | 0.30 |  | 0.77 |  | 0.70 |  | <0.001 |  |
| CaOx |  |  |  |  |  |  |  |  |  |  |  |
| Overall | 36 | 1099 ± 239 | 635-1522 | 514 ± 116 | 304-827 | 585 ± 203 | 227-945 | 52.1 ± 10.6% | 29.5-73.6% | 147 ± 57 | 48-260 |
| ≤10 mm | 25 | 1024 ± 219 | 935-1367 | 480 ± 109 | 304-793 | 543 ± 201 | 227-929 | 51.7 ± 11.5% | 29.5-73.6% | 175 ± 41 | 116-260 |
| >10 mm | 11 | 1270 ± 197 | 792-1522 | 590 ± 98 | 441-827 | 679 ± 180 | 321-945 | 52.8 ± 8.7% | 31.1-63.7% | 88 ± 30 | 48-132 |
| Intra CaOx comparison* |  | 0.01 |  | <0.001 |  | 0.03 |  | 0.92 |  | <0.001 |  |
| Inter Group comparison‡ |  | <0.001 for all |  | <0.001 for all |  | <0.001 for all |  | <0.001 for all |  | <0.001 for all |  |

From this data, the inventors have determined that a combination of core and peripheral HU evaluation in addition to an evaluation of homogeneity on bone windows may provide added discriminatory value, particularly for those stones with HU values of 400-800, where there is overlap between UA and calcium stone compositions.

Figure 2:
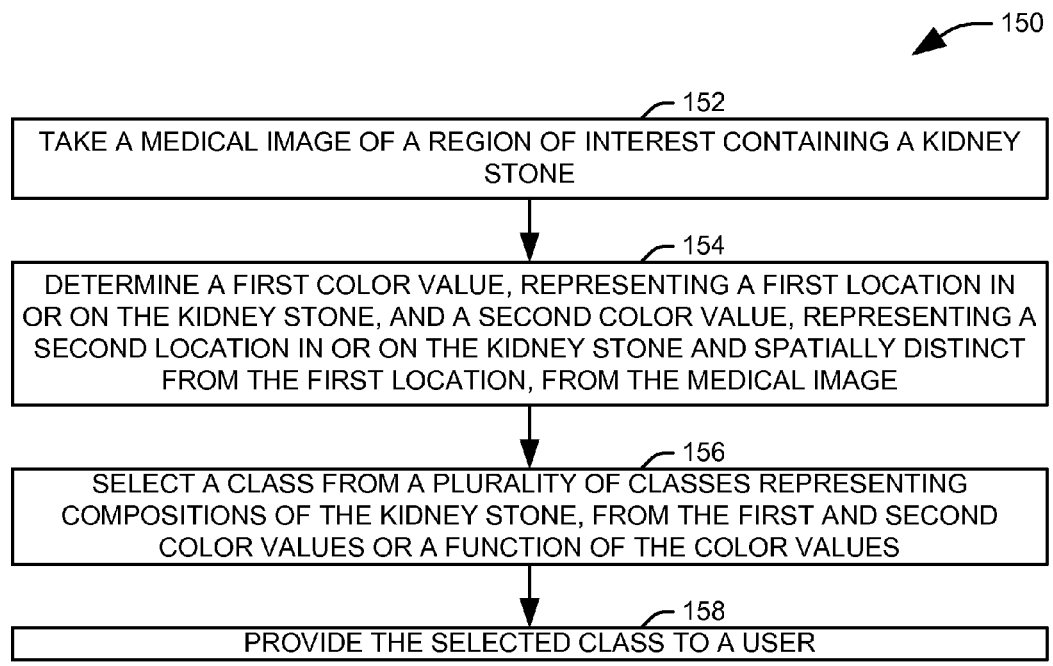
FIG. 2 illustrates one method for determining a composition of a kidney stone from medical imaging.

In view of the foregoing structural and functional features described above, methods in accordance with various aspects of the present invention will be better appreciated with reference to FIGS. 2 and 3. While, for purposes of simplicity of explanation, the methods of FIGS. 2 and 3 are shown and described as executing serially, it is to be understood and appreciated that the present invention is not limited by the illustrated order, as some aspects could, in accordance with the present invention, occur in different orders and/or concurrently with other aspects from that shown and described.

FIG. 2 illustrates a method 100 for determining a composition of a kidney stone from medical imaging in accordance with an aspect of the present invention. At 102, a medical is taken of a region of interest containing a kidney stone. At 104, a first color value, representing a first location in or on the kidney stone, and a second color value, representing a second location in or on the kidney stone, are determined from the CT scan. It will be appreciated that the first and second locations are selected to be spatially distinct. These attenuation values, along with other data determined from the CT scan, can be used as a plurality of features for a classifier. At 106, a class is selected from a plurality of classes, each representing a possible composition of the kidney stone, using at least the first and second attenuation values or a function of these values. For example, the attenuation values or a function of the attenuation values can be provided as a feature to an associated classifier system. Potential features can include, for example, a ratio of first and second attenuation values, a difference between the first and second attenuation values, a relative difference (e.g., a ratio of the difference to one of the attenuation values), or a normalized difference (a ratio of the difference to a largest transverse diameter of the stone. At 108, the selected class is provided to a user in a human comprehensible form.

interest containing a kidney stone. At 154, a first attenuation value, representing a central region of the kidney stone, and a second attenuation value, representing at least one peripheral region of the kidney stone, are determined from the CT scan. These attenuation values, along with other data determined from the CT scan, can be used as a plurality of features for a classifier. At 156, a class is selected from a plurality of classes, each representing a possible composition of the kidney stone, using at least the first and second attenuation values or a function of these values. Potential functions can include, for example, a ratio of first and second attenuation values, a difference between the first and second attenuation values, a relative difference (e.g., a ratio of the difference to one of the attenuation values), or a normalized difference (a ratio of the difference to a largest transverse diameter of the stone. In one implementation, the plurality of classes can include a uric acid stone class and a calcium-containing stone class. At 158, the selected class is provided to a user in a human comprehensible form.

Figure 4:
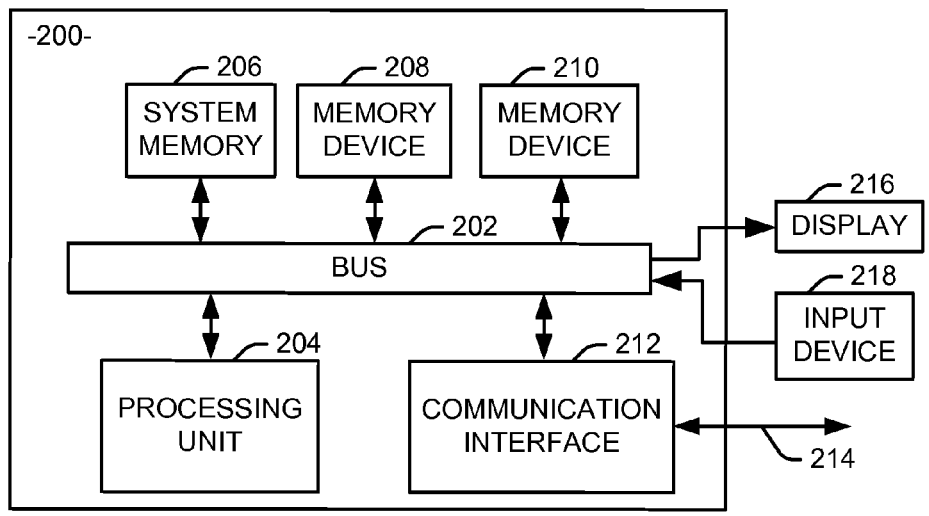
FIG. 4 is a schematic block diagram illustrating an exemplary system of hardware components capable of implementing examples of the systems and methods disclosed in FIGS. 1-3.

FIG. 4 is a schematic block diagram illustrating an exemplary system 200 of hardware components capable of implementing examples of the systems and methods disclosed in FIGS. 1-3, such as the imager interface 12, feature extractor 14, classifier 16, and user interface 18 illustrated in FIG. 1. The system 200 can include various systems and subsystems. The system 200 can be a personal computer, a laptop computer, a workstation, a computer system, an appliance, an application-specific integrated circuit (ASIC), a server, a server blade center, a server farm, etc.

The system 200 can includes a system bus 202, a processing unit 204, a system memory 206, memory devices 208 and 210, a communication interface 212 (e.g., a network interface), a communication link 214, a display 216 (e.g., a video screen), and an input device 218 (e.g., a keyboard and/or a mouse). The system bus 202 can be in communication with the processing unit 204 and the system memory 206. The additional memory devices 208 and 210, such as a hard disk drive, server, stand alone database, or other non-volatile memory, can also be in communication with the system bus 202. The system bus 202 interconnects the processing unit 204, the memory devices 206-210, the communication interface 212, the display 216, and the input device 218. In some examples, the system bus 202 also interconnects an additional port (not shown), such as a universal serial bus (USB) port.

The processing unit 204 can be a computing device and can include an application-specific integrated circuit (ASIC). The processing unit 204 executes a set of instructions to implement the operations of examples disclosed herein. The processing unit can include a processing core.

The additional memory devices 206, 208 and 210 can store data, programs, instructions, database queries in text or compiled form, and any other information that can be needed to operate a computer. The memories 206, 208 and 210 can be implemented as computer-readable media (integrated or removable) such as a memory card, disk drive, compact disk (CD), or server accessible over a network. In certain examples, the memories 206, 208 and 210 can comprise text, images, video, and/or audio, portions of which can be available in formats comprehensible to human beings.

Additionally or alternatively, the system 200 can access an external data source or query source through the communication interface 212, which can communicate with the system bus 202 and the communication link 214.

In operation, the system 200 can be used to implement one or more parts of a diagnostic system in accordance with the present invention. Computer executable logic for implementing the diagnostic system resides on one or more of the system memory 206, and the memory devices 208, 210 in accordance with certain examples. The processing unit 204 executes one or more computer executable instructions originating from the system memory 206 and the memory devices 208 and 210. The term "computer readable medium" as used herein refers to a medium that participates in providing instructions to the processing unit 204 for execution, and can, in practice, refer to multiple, operatively connected apparatuses for storing machine executable instructions.

What have been described above are examples of the present invention. It is, of course, not possible to describe every conceivable combination of components or methodologies for purposes of describing the present invention, but one of ordinary skill in the art will recognize that many further combinations and permutations of the present invention are possible. Accordingly, the present invention is intended to embrace all such alterations, modifications and variations that fall within the spirit and scope of the appended claims.

The invention claimed is:

1. A non-transitory computer readable medium storing machine executable instructions that, when executed by an associated processor, provide a system for determining the composition of a kidney stone from a medical image, the system comprising:
    a feature extractor configured to provide a plurality of features from the medical image, the plurality of features comprising either a pair of an attenuation values, including a first attenuation value from a first location in or on the kidney stone and a second attenuation value from a second location in or on the kidney stone, or a function of the first and second attenuation values, with the second location being spatially distinct from the first location;
    a classifier configured to select one of a plurality of classes for the kidney stone, each class representing a specific constituent material, from the plurality of features; and
    a user interface configured to display the class to a user in a human comprehensible form.

2. The non-transitory computer readable medium of claim 1, wherein the medical image is a bone-windowed computed tomography image.

3. The non-transitory computer readable medium of claim 2, wherein the first and second locations are drawn from a transverse slice of the bone-windowed computed tomography image having the two largest transverse diameters.

4. The non-transitory computer readable medium of claim 1, wherein the first location is a core of the kidney stone and the second location is a periphery of the kidney stone.

5. The non-transitory computer readable medium of claim 1, the plurality of features comprising a ratio of the first and second attenuation values.

6. The non-transitory computer readable medium of claim 1, the plurality of features comprising a difference between of the first and second attenuation values.

7. The non-transitory computer readable medium of claim 1, the plurality of features comprising a ratio of a difference between the first and second attenuation values to one of the first and second values.

8. The non-transitory computer readable medium of claim 1, the plurality of features comprising a ratio of the difference between the first and second attenuation values to a largest transverse diameter of the kidney stone.

9. The non-transitory computer readable medium of claim 1, wherein the plurality of features comprises at least one of a volume of the kidney stone, a diameter of a selected cross-section, a largest transverse diameter, and a variance of the attenuation values in a selected cross-section.

10. A system for determining the composition of a kidney stone comprising:
    a computed tomography imager;
    a processor;
    an output device; and
    a non-transitory computer readable medium storing machine executable instructions and operatively connected to the processor, the machine executable instructions comprising:
    imager interface configured to receive a computed tomography image from the computed tomography imager and provide a bone-windowed computed tomography image from the received computed tomography image;
    a feature extractor configured to provide a plurality of features from the bone-windowed computed tomography image, the plurality of features comprising either a pair of an attenuation values, including a first attenuation value from a first location in or on the kidney stone and a second attenuation value from a second location in or on the kidney stone, or a function of the first and second attenuation values, with the second location being spatially distinct from the first location;
    a classifier configured to select one of a plurality of classes for the kidney stone from the plurality of features, each class representing a specific constituent material; and
    a user interface configured to display the class to a user in a human comprehensible form.

11. The system of claim 10, wherein the first and second locations are drawn from a transverse slice of the bone-windowed computed tomography image having the two largest transverse diameters.

12. The system of claim 11, the plurality of features comprising a ratio of the difference between the first and second attenuation values to the largest transverse diameter of the kidney stone.

13. The system of claim 10, wherein the first location is a core of the kidney stone and the second location is a periphery of the kidney stone.

14. The system of claim 10, wherein the plurality of features comprises at least one of a volume of the kidney stone, a diameter of a selected cross-section, a largest transverse diameter, and a variance of the attenuation values in a selected cross-section.

15. A method for determining the composition of a kidney stone comprising:
   obtaining a computed tomography (CT) scan of a region of interest containing a kidney stone at an associated CT imaging system;
   determining a first attenuation value, representing a central region of the kidney stone, and a second attenuation value, representing at least one peripheral region of the kidney stone, from the CT scan;
   selecting a class from a plurality of classes each representing a possible composition of the kidney stone, using at least the first and second attenuation values; and
   providing the selected class to a user in a human comprehensible form.

16. The method of claim 15, wherein selecting a class from a plurality of classes using at least the first and second attenuation values comprises providing the first and second attenuation values to an associated classifier system.

17. The method of claim 15, wherein selecting a class from a plurality of classes using at least the first and second attenuation values comprises calculating a ratio of the first and second attenuation values and selecting the class according to the determined ratio.

18. The method of claim 15, wherein selecting a class from a plurality of classes using at least the first and second attenuation values comprises calculating a difference between the first and second attenuation values and selecting the class according to the determined difference.

19. The method of claim 15, wherein selecting a class from a plurality of classes using at least the first and second attenuation values comprises calculating a relative difference between the first and second attenuation values as a ratio of a difference between the first and second attenuation values and selecting the class according to the determined relative difference.

20. The method of claim 15, wherein selecting a class from a plurality of classes using at least the first and second attenuation values comprises calculating a normalized difference between the first and second attenuation values as a ratio of the difference between the first and second attenuation values to a largest transverse diameter of the kidney stone and selecting the class according to the determined normalized difference.

* * * * *